United States Patent [19]

Mizuno et al.

[11] Patent Number: 4,462,984

[45] Date of Patent: * Jul. 31, 1984

[54] SUPPOSITORY BASE COMPOSITION

[75] Inventors: Mitsuo Mizuno, Yokosuka; Akinori Suginaka, Kamakura; Masahiko Fujii, Tokyo; Shinichi Akimoto, Machida, all of Japan

[73] Assignee: Nippon Oil and Fats Company, Ltd., Tokyo, Japan

[*] Notice: The portion of the term of this patent subsequent to Jan. 11, 2000 has been disclaimed.

[21] Appl. No.: 425,101

[22] Filed: Sep. 27, 1982

Related U.S. Application Data

[63] Continuation of Ser. No. 198,581, Oct. 20, 1980, Pat. No. 4,368,185.

[30] Foreign Application Priority Data

Oct. 26, 1979 [JP] Japan ............................ 54-138562

[51] Int. Cl.$^3$ ................................................ A61K 9/02
[52] U.S. Cl. ....................................... 424/78; 424/365
[58] Field of Search .................. 424/78, 365, DIG. 15

[56] References Cited

U.S. PATENT DOCUMENTS 2,538,127 1/1951 Saunders et al. ............ 424/DIG. 15
2,975,099 3/1961 Goyan et al. ................ 424/DIG. 15
3,767,801 10/1973 Tuma et al. ......................... 424/230
4,368,185 1/1983 Mizuno et al. ........................ 424/78

FOREIGN PATENT DOCUMENTS 2732929 2/1979 Fed. Rep. of Germany .
54-157820 12/1979 Japan .
1384760 2/1975 United Kingdom .
1462399 1/1977 United Kingdom .

OTHER PUBLICATIONS

Chem. Abstracts 92, #220693t, (1980) of Japan Kokai Tokkyo Koho, 79, 157820.
Lachman et al., The Theory & Practice of Industrial Pharmacy, 2nd Ed., (1976), Lea & Febiger, Phila., Pa., "Suppositories", pp. 245–269, Semi-Solids, pp. 215–244, Emulsions, pp. 184–214.

Primary Examiner—Shep K. Rose
Attorney, Agent, or Firm—Parkhurst & Oliff

[57] ABSTRACT

A suppository base composition comprising 5–80% by weight of polyethylene glycol, 5–80% by weight of triglyceride of fatty acid having 6–22 carbon atoms and 5–80% by weight of a specifically limited alkylene oxide derivative has a melting point of 30°–60° C., a compatibility with both of a polar drug component and a non-polar drug component, and can provide suppositories having excellent moldability and storage stability.

1 Claim, No Drawings

SUPPOSITORY BASE COMPOSITION

This is a continuation of application Ser. No. 198,581 filed Oct. 20, 1980, now U.S. Pat. No. 4,368,185.

BACKGROUND OF THE INVENTION (1) Field of the Invention

The present invention relates to a suppository base composition.

(2) Description of the Prior Art

A suppository is smaller than other medicinal preparations for internal use in the amount of drug component to be decomposed by the action of acid, alkali, digestive enzymes and the like in the digestive fluid, and further does not cause gastroenteric troubles. Particularly, a suppository has merit in that it can be easily dosed to children. Moreover, when a systemic dosage of a medicine by injection causes serious ill effects, the ill effects can be decreased by a local dosage of a suppository only to the diseased portion, and further the human body can be free from the pain at the injecton.

There are mainly used two kinds of suppository bases of polyethylene glycol (hereinafter, abbreviated as PEG) and triglyceride (hereinafter, abbreviated as TG) of fatty acid at present.

Both PEG and TG are excellent suppository bases, but when a suppository is produced by the use of highly hydrophilic PEG, only a highly polar drug component, which dissolves in PEG or disperses uniformly therein, can be used. On the other hand, when a suppository is produced by the use of TG, which is highly lipophilic, only a non-polar drug component which dissolves in TG or disperses uniformly therein can be used. Moreover, PEG and TG have no compatibility with each other, and therefore they cannot be used in admixture, and it accordingly is difficult to use a polar drug component in combination with a non-polar drug component.

Further, in the suppository using TG, the suppository is melted by the body temperature to absorb the drug component into the human body. Therefore, the melting point of the suppository is set to a temperature near the body temperature, and the suppository possesses poor strength at high temperatures. Therefore, it is necessary to store the suppository in a cold and dark place in order to prevent deformation of shape, and the suppository has a risk of melting during its transportation.

The inventors have made various investigations in order to produce suppository bases free from these drawbacks, and found out that a specifically limited alkylene oxide derivative is excellent as a suppository base and is able to mix PEG and TG, and invented a novel suppository base containing these three components.

SUMMARY OF THE INVENTION

The feature of the present invention is to provide a suppository base composition comprising 5–80% by weight of PEG having an average molecular weight of 200–20,000, 5–80% by weight of TG of fatty acid having 6–22 carbon atoms and 5–80% by weight of a compound having the following general formula (1), whose hydroxyl groups may be partly or wholly esterified:

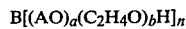

$$B[(AO)_a(C_2H_4O)_bH]_n \qquad (1)$$

wherein B represents a residue of a compound having 1–8 active hydrogen atoms, A reprresents $C_3H_6$ or $C_4H_8$ alone or in admixture, a represents an integer of 15–50, b represents an integer of 20–200, n represents an integer of 1–8, and having an average molecular weight of at least 2,500 per one functional group.

DESCRIPTION OF THE PREFERRED EMBODIMENT

PEGs to be used in the present invention are ones having an average molecular weight of 200–20,000.

TGs of fatty acid having 6–22 carbon atoms to be used in the present invention are TGs of caproic acid, caprilic acid, capric acid, lauric acid, myristic acid, palmitic acid, stearic acid, oleic acid, arachic acid, behenic acid and the like. These TGs are used alone or in admixture.

The compounds having the above described general formula (1) are compounds obtained by adding a given amount of alkylene oxide to a compound having 1–8 active hydrogen atoms.

The compounds having 1–8 active hydrogen atoms include methyl alcohol, ethyl alcohol, butyl alcohol, octyl alcohol, lauryl alcohol, myristyl alcohol, cetyl alcohol, stearyl alcohol, oleyl alcohol, isostearyl alcohol, dimeric acohols formed by a Guerbet process, ethylene glycol, propylene glycol, butylene glycol, hexylene glycol, dodecane diol, hexadecane diol, octadecane diol, glycerine, trimethylolethane, trimethylolpropane, 1,3,5-pentane triol, erythritol, pentaerythritol, diglycerine, triglycerine, dipentaerythritol, sorbitol, sorbitan, sorbide, glucose, fructose, mannose, xylose, methyl glucoside, trehalose, sucrose, ethylenediamine and the like.

The addition amount of alkylene oxides to the above described compound having 1–8 active hydrogen atoms is such that propylene oxide, butylene oxide or tetrahydrofuran or mixture thereof is added to the compound in an amount of 15–50 moles per functional group of the compound and ethylene oxide is added to the compound in an amount of 20–200 moles per functional group of the compound. Moreover, it is necessary that the resulting addition product having the above described general formula (1) has an average molecular weight of at least 2,500 per functional group. When the addition amount of the alkylene oxides is smaller than the above described amount, the resulting addition product having the above described general formula (1) can not be able to mix homogeneously PEG and TG. When the addition amount exceeds the above described amount, the addition product has an excessively high melting point and viscosity and is difficult to handle in the formulation of a small size suppository. The compound having the general formula (1) has such an excellent property that the compound can dissolve or disperse more easily than PEG and TG, and that the compound can mix PEG and TG in an optimal mixing ratio. The compound having the general formula (1) has a melting point of 10°–70° C., and when PEG and TG to be compounded with the compound are properly selected, suppository base compositions having an optimal melting point can be produced.

The suppository base composition of the present invention is a homogeneous mixture consisting of 5–80% by weight, respectively, of the above described three components of PEG, TG and the compound having the general formula (1). When the amount of any one of the above described three components exceeds 80% by weight, the drawbacks of the respective three components appear. When the amount of any one of the three components is smaller than 5% by weight, the mixing effect of the three components does not appear. Particularly, when the amount of the compound having the general formula (1) is smaller than 5% by weight, PEG can not be homogeneously mixed with TG, and separates from TG. It is preferable that the ethylene oxide chain of the compound having the general formula (1) occupy 40–90% of the total molecular weight of that compound; and that the compound of general formula (1) have an average molecular weight of 3,000–9,000 per functional group. It is also preferable that the residue B be a residue of an alcohol or glycol having 1–22 carbon atoms.

The suppository base composition of the present invention contains both a hydrophilic component and a lipophilic component, and therefore the composition can be used as a base for both a polar drug component and a non-polar drug component, and suppository base compositions having a melting point of 30°–60° C. can be produced. Therefore, the suppository base composition can be widely used, and the resulting suppository is very excellent in the moldability and storage stability.

The suppository base composition of the present invention may contain water, propylene glycol, glycerine, propylene glycol fatty acid ester, sucrose fatty acid ester, sorbitan fatty acid ester, polyoxethylene alkyl ether, polyoxyethylene polyhydric alcohol fatty acid ester and oil-soluble polyoxyalkylene glycol derivative in order to lower its viscosity during production, to adjust its melting point, to improve its lubricating property at the insertion of the suppository into the human body and to promote the liberation of the drug component.

The following examples are given for the purpose of illustration of this invention and are not intended as limitations thereof. In the examples, "%" means % by weight.

EXAMPLE 1

Suppository base compositions shown in the following Table 2 were prepared by the use of PEG, TG and a compound having the general formula (1) shown in the following Table 1, and a compatibility test of the compositions was carried out.

Test method and evaluation method

Into a beaker of 300 ml capacity is charged 100 g of a sample composition, which is stirred at 60° C. until the composition becomes homogeneous. When the composition has become homogeneous, the stirring is stopped, and the beaker is cooled to 20° C. to solidify the composition.

The composition is evaluated according to the following standard.

o . . . homogeneously solidified composition
x . . . two or more separated layers or inhomogeneously solidified composition.

The tested compositions and the test results are shown in Table 2.

It can be seen from Table 2 that all the suppository base compositions of the present invention, which are prepared by the use of the compound having the general formula (1), have homogeneously solidified, and have good compatibility.

TABLE 1

| Compound used in the test | |
|---|---|
| 1. PEG*5 | average molecular weight |
| PEG #300 | 300 |
| PEG #400 | 400 |
| PEG #1540 | 1500 |
| PEG #4000 | 3000 |
| PEG #6000 | 9000 |
| 2. TG | composition of alkyl groups |
| TG - A | $C_8$: 85%, $C_{10}$: 15% |
| TG - B | $C_{12}$: 50%, $C_{14}$: 23%, $C_{16}$: 14%, $C_{18}$: 13% |
| TG - C | $C_{12}$: 42%, $C_{14}$: 18%, $C_{16}$: 17%, $C_{18}$: 23% |
| TG - D | $C_{12}$: 68%, $C_{14}$: 10%, $C_{16}$: 11%, $C_{18}$: 11% |
| 3. Compound having the general formula (1) | |
| C - 1 | $C_{16}H_{33}O(C_3H_6O)_{30}(C_2H_4O)_{25}H$ |
| C - 2 | $C_{18}H_{37}O(C_3H_6O)_{30}(C_2H_4O)_{40}H$ |
| C - 3 | $C_{24}H_{49}O(C_3H_6O)_{25}(C_2H_4O)_{50}H$ |
| C - 4*1 | $P[(C_3H_6O)_{17}(C_2H_4O)_{50}H]_2$ |
| C - 5 | $P[(C_3H_6O)_{25}(C_2H_4O)_{70}H]_2$ |
| C - 6 | $P[(C_3H_6O)_{35}(C_2H_4O)_{100}H]_2$ |
| C - 7 | $P[(C_4H_8O)_2(C_3H_4O)_{60}COC_{11}H_{28}]_2$ |
| C - 8*2 | $D[(C_3H_6O)_{40}(C_2H_4O)_{120}H]_2$ |
| C - 9*3 | $G[(C_3H_6O)_{30}(C_2H_4O)_{70}H]_3$ |
| C - 10*4 | $S[(C_3H_6O)_{30}(C_2H_4O)_{80}H]_6$ |
| 4. Other compound | |
| D - 1 | $C_{16}H_{33}O(C_2H_4O)_{25}H$ |
| D - 2 | $C_{15}H_{37}O(C_3H_6O)_{30}(C_2H_4O)_3H$ |
| D - 3*1 | $P[(C_3H_6O)_{10}(C_2H_4O)_{15}H]_2$ |
| D - 4 | polyoxyethylene(20)-sorbitan monooleate |
| D - 5 | polyoxyethylene(70)-pentaerythritol tristearate |
| D - 6 | glycerine monostearate |
| D - 7 | propylene glycol |

TABLE 1-continued

| Compound used in the test | |
|---|---|
| D - 8 | water |

Note
*[1] P means propyleneglycol residue
*[2] D means dodecanediol residue
*[3] G means glycerine residue
*[4] S means sorbitol residue
*[5] PEGs #300, #400, #1540, #4000 and #6000 are trademarks of PEGs sold by Nippon Oil and Fats Company Ltd.

TABLE 2

Results of compatibility test

| | Test No. | PEG Compound | % | TG Compound | % | Compound having the general formula (1) Compound | % | Other compound Compound | % | Evaluation | Melting point (°C.) |
|---|---|---|---|---|---|---|---|---|---|---|---|
| Composition according to the present invention | 1 | #6000 | 30 | TG-B | 30 | C-1 | 40 | — | — | o | 48 |
| | 2 | " | 30 | " | 30 | C-2 | 40 | — | — | o | 52 |
| | 3 | " | 35 | " | 35 | C-3 | 30 | — | — | o | 50 |
| | 4 | " | 30 | " | 20 | C-4 | 50 | — | — | o | 46 |
| | 5 | " | 30 | " | 20 | C-5 | 50 | — | — | o | 50 |
| | 6 | " | 40 | " | 40 | C-6 | 20 | — | — | o | 55 |
| | 7 | " | 40 | " | 30 | C-7 | 30 | — | — | o | 50 |
| | 8 | " | 30 | " | 30 | C-8 | 40 | — | — | o | 54 |
| | 9 | " | 30 | " | 30 | C-9 | 40 | — | — | o | 52 |
| | 10 | " | 30 | " | 30 | C-10 | 40 | — | — | o | 52 |
| | 11 | #400 | 35 | TG-C | 35 | C-6 | 30 | — | — | o | 46 |
| | 12 | #400 | 35 | TG-D | 35 | C-6 | 30 | — | — | o | 46 |
| | 13 | #6000 | 25 | TG-D | 5 | C-2 | 70 | — | — | o | 52 |
| | 14 | #6000 | 5 | TG-D | 25 | C-5 | 70 | — | — | o | 50 |
| | 15 | { #300 / #1540 | 20 / 20 | TG-C | 30 | { C-3 / C-6 | 29 / 10 | — | — | o | 50 |
| | 16 | #400 | 30 | TG-A | 30 | { C-2 / C-6 | 20 / 20 | — | — | o | 43 |
| | 17 | { #400 / #4000 | 20 / 10 | TG-D | 40 | { C-2 / C-8 | 20 / 10 | — | — | o | 45 |
| | 18 | { #400 / #4000 | 20 / 10 | TG-C | 35 | { C-2 / C-6 | 20 / 10 | D-1 | 5 | o | 45 |
| | 19 | { #400 / #4000 | 30 / 30 | TG-B | 7 | { C-6 / C-10 | 20 / 5 | D-2 | 8 | o | 47 |
| | 20 | { #400 / #4000 | 5 / 5 | TG-C | 68 | { C-2 / C-6 | 5 / 15 | D-3 | 2 | o | 45 |
| | 21 | #1540 | 35 | TG-D | 40 | C-6 | 20 | D-4 | 5 | o | 55 |
| | 22 | #4000 | 30 | TG-C | 25 | [ C-2 / C-6 | 20 / 15 | D-5 | 10 | o | 52 |
| | 23 | #4000 | 30 | TG-C | 30 | C-6 | 35 | D-6 | 5 | o | 52 |
| | 24 | " | 30 | " | 30 | " | 35 | D-7 | 5 | o | 48 |
| | 25 | " | 30 | " | 30 | " | 35 | D-8 | 5 | o | 46 |
| Comparative Composition | 26 | #6000 | 25 | TG-B | 25 | — | — | D-1 | 50 | x | — |
| | 27 | " | " | " | " | — | — | 2 | " | x | — |
| | 28 | " | " | " | " | — | — | 3 | " | x | — |
| | 29 | " | " | " | " | — | — | 4 | " | x | — |
| | 30 | " | " | " | " | — | — | 5 | " | x | — |
| | 31 | #6000 | 15 | TG-B | 15 | — | — | D-1 | 70 | x | — |
| | 32 | " | " | " | " | — | — | 2 | " | x | — |
| | 33 | " | " | " | " | — | — | 3 | " | x | — |
| | 34 | " | " | " | " | — | — | 4 | " | x | — |
| | 35 | " | " | " | " | — | — | 5 | " | x | — |

EXAMPLE 2

A mixture of 5 g of a drug component and 75 g of a suppository base composition shown in the following Table 3 was melted at 70° C. The melted mixture, after being fully stirred, was filled in a container pack of 2.5 g capacity for a suppository. The storage stability of the resulting suppositories was measured after the suppositories were kept at 5° C., 20° C. or 35° C. for 2 weeks; or kept at 5° C. and at 40° C. on alternate days for two weeks, and was evaluated according to the following standard:

o . . . Original homogeneous state was maintained.
x . . . Crystals of drug component grew, and the suppository became inhomogeneous.
xx . . . Almost all the drug component was separated.

The following Table 3 shows the results of the test.

It can be seen from Table 3 that the suppository of the present invention always maintains a homogeneous state within the temperature range of 5°–70° C. and has a good storage stability.

TABLE 3

Storage stability test for suppository

| Drug component | Base composition | 70° C. (at the formulation) | 5° C. | 20°C. | 35° C. | 5° C. and 40° C. on alternate days |
|---|---|---|---|---|---|---|
| Indomethacin | *No. 11 composition in Table 2 | homogeneous transparent liquid | o | o | o | o |
| | *No. 18 composition in Table 2 | homogeneous transparent liquid | o | o | o | o |
| | PEG #1540 75% PEG #4000 25% | homogeneous transparent liquid | x | x | x | x |
| | TG-B 50% TG-C 50% | substantially homogeneous dispersion | o | o | x | xx |
| Acetylsalicylic acid | *No. 12 composition in Table 2 | homogenous transparent liquid | o | o | o | o |
| | *No. 20 composition in Table 2 | homogenous transparent liquid | o | o | o | o |
| | PEG #400 10% PEG #4000 90% | homogeneous transparent liquid | x | o | o | o |
| | TG-B 40% TD-D 60 | substantially homogeneous dispersion | o | o | o | xx |
| Ergosterol | *No. 6 composition in Table 2 | homogeneous transparent liquid | o | o | o | o |
| | *No. 16 composition in Table 2 | homogeneous transparent liquid | o | o | o | o |
| | REG #1540 80% Reg #6000 20% | substantially homogeneous transparent liquid | x | x | o | o |
| | TG-C 50% TG-D 50% | substantially homogeneous dispersion | o | o | x | xx |

Note:
Among the base compositions, base compositions indicated by the mark * are those according to the present invention, and base compositions having no mark are comparative compostions.

What is claimed is:

1. A molded, storage-stable suppository base composition, stable in a temperature range of from 5 degrees C. to 70 degrees C., comprising 5–80% by weight of polyethylene glycol having an average molecular weight of 200–20,000, 5–80% by weight of triglyceride of fatty acid having 6–22 carbon atoms and 5–80% by weight of a compound having the following general formula (1), whose hydroxyl group may be partly or wholly esterified, $$B[(AO)_a(C_2H_4O)_bH]_n \quad (1)$$

wherein B represents a residue of an alcohol or polyol having 1–8 active hydrogen atoms, A represents $C_3H_6$ or $C_4H_8$ alone or in admixture, a represents an integer of 15–50, b represents an integer of 20–200 and n represents an integer of 1–8, and having an average molcular weight of at least 2,500 per one functional group, said suppository composition being substantially homogeneous in liquid and solid states.

* * * * *